United States Patent
Eun Park et al.

(10) Patent No.: US 8,404,182 B2
(45) Date of Patent: Mar. 26, 2013

(54) STERILIZING METHOD, STERILIZING APPARATUS, AND AIR CLEANING METHOD AND APPARATUS USING THE SAME

(75) Inventors: Rae Eun Park, Suwon (KR); Jun Hyoun Kwon, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 170 days.

(21) Appl. No.: 12/541,448

(22) Filed: Aug. 14, 2009

(65) Prior Publication Data

US 2010/0003166 A1    Jan. 7, 2010

Related U.S. Application Data

(62) Division of application No. 11/149,361, filed on Jun. 10, 2005, now Pat. No. 7,691,335.

(30) Foreign Application Priority Data

Jul. 27, 2004    (KR) ................................ 2004-058861

(51) Int. Cl.
*A61L 2/00* (2006.01)
*A61L 2/18* (2006.01)
*A61L 9/00* (2006.01)
*B01J 7/00* (2006.01)

(52) U.S. Cl. ............. 422/22; 422/28; 422/29; 422/292; 422/305; 422/306

(58) Field of Classification Search ............... 422/22, 422/28, 29, 292, 305, 306; 205/701
See application file for complete search history.

(56) References Cited

U.S. PATENT DOCUMENTS

| | | | |
|---|---|---|---|
| 3,942,072 A | 3/1976 | Best et al. | |
| 4,708,803 A * | 11/1987 | Ostreicher et al. | 210/650 |
| 4,711,793 A * | 12/1987 | Ostreicher et al. | 427/244 |
| 5,198,336 A * | 3/1993 | Knobeloch et al. | 435/4 |
| 5,368,708 A * | 11/1994 | Pankow | 205/688 |
| 5,741,352 A * | 4/1998 | Ford et al. | 96/68 |
| 6,350,417 B1 | 2/2002 | Lau et al. | |
| 6,850,403 B1 | 2/2005 | Gefter et al. | |
| 6,878,287 B1 * | 4/2005 | Marais | 210/748.17 |
| 2005/0170011 A1* | 8/2005 | Yanagihara et al. | 424/600 |
| 2006/0227491 A1* | 10/2006 | Rosati et al. | 361/229 |
| 2007/0017801 A1* | 1/2007 | Fukui et al. | 204/230.2 |
| 2007/0254349 A1* | 11/2007 | Vizethum et al. | 435/173.1 |
| 2008/0093210 A1* | 4/2008 | Edwards | 204/157.3 |
| 2009/0266706 A1* | 10/2009 | Fukui et al. | 204/229.8 |

FOREIGN PATENT DOCUMENTS

| | | |
|---|---|---|
| EP | 1625890 A2 | 2/2006 |
| EP | 1 791 232 A1 | 5/2007 |
| JP | 2001-56395 A | 2/2001 |
| JP | 2003-007426 A | 1/2003 |

(Continued)

OTHER PUBLICATIONS

Search Report dated May 5, 2010 from the European Patent Office in counterpart application No. 08020908.3.

(Continued)

*Primary Examiner* — Regina M. Yoo
(74) *Attorney, Agent, or Firm* — Sughrue Mion, PLLC (57) ABSTRACT

A sterilizing method and apparatus in which neutral atoms and anions are coupled to produce a sterilizing substance which is, in turn, used to remove an object to be removed by sterilization. The sterilizing apparatus includes a cation generator and an anion generator, which are separate from each other. Also disclosed as an air cleaning method and apparatus using the sterilizing method and apparatus.

5 Claims, 12 Drawing Sheets

FOREIGN PATENT DOCUMENTS

| | | |
|---|---|---|
| JP | 2003-123940 A | 4/2003 |
| JP | 2003-153995 A | 5/2003 |
| JP | 2003-210564 A | 7/2003 |
| JP | 2004-79273 A | 3/2004 |
| JP | 2004-192944 A | 7/2004 |
| JP | 2004-363088 A | 12/2004 |
| JP | 2005-116229 A | 4/2005 |
| KR | 10-1991-0014998 B1 | 8/1991 |
| KR | 10-2003-0036134 A | 5/2003 |
| WO | WO 01/56616 A2 * | 8/2001 |
| WO | 2005077523 A1 | 8/2005 |

OTHER PUBLICATIONS

Japanese Abstract No. 2005116229, dated Apr. 28, 2005.

* cited by examiner

STERILIZING METHOD, STERILIZING APPARATUS, AND AIR CLEANING METHOD AND APPARATUS USING THE SAME

CROSS-REFERENCE TO RELATED APPLICATION

This is a Divisional application of U.S. application Ser. No. 11/149,361 filed Jun. 10, 2005, now U.S. Pat. No. 7,691,335, which claims priority from Korean Patent Application No.2004-58861, filed on Jul. 27, 2004. The disclosures of each of the above applications are incorporated herein by reference in their entirety.

BACKGROUND OF THE INVENTION

1. Field of the Invention

The present invention relates to a sterilizing method and apparatus, and, more particularly, to a sterilizing method and apparatus for killing bacteria by generating ions. The present invention also relates to an air cleaning method and apparatus using the sterilizing method and apparatus.

2. Description of the Related Art

Generally, an air cleaning apparatus includes a filter mounted in a housing for filtering diverse impurities; a blowing fan for introducing air from a room space into the housing, thereby forcing the introduced air to pass through the filter, and for discharging the filtered air out of the housing; and an anion generator for generating anions.

In this air cleaning apparatus, the room air is cleaned while passing through the filter when the blowing fan is driven, and is then discharged into the room space, together with anions generated from the anion generator. However, such a conventional air cleaning apparatus, which includes a filter and an anion generator, is limited in its ability to kill bacteria floating in the air, using only the filter and anions generated from the anion generator. In order to solve this problem, a new ion generator has been proposed which performs sterilization using both anions and cations. Such an ion generator, which can generate both anions and cations, is described in Japanese Patent Laid-open Publication No. 2003-123940.

In this conventional ion generator, AC voltage is applied to two electrodes to alternately generate anions and cations. The generated anions and cations are supplied into a room space. In this case, the cations are hydrogen ions (H+), and the anions are super-oxide anions ($O_2^-$). When the hydrogen ions and super-oxide anions are supplied into the room space, they produce hydroxyl radicals (OH) or hydrogen peroxide ($H_2O_2$). These compounds are adsorbed to bacteria present in the room air, to thereby oxidize and kill the bacteria.

However, this conventional ion generator has a problem in that hydrogen ions, which are harmful to the human body, are discharged into the room space intact, so that the user's health may be negatively impacted upon inhaling the hydrogen ions.

Furthermore, since each electrode alternately generates anions and cations, considerable amounts of anions and cations are coupled before they can be used for sterilization, so that their effectiveness is lost.

In addition, since each electrode alternately generates anions and cations, it is impossible to generate sufficient amounts of anions and cations required for sterilization within a short period of time.

SUMMARY OF THE INVENTION

The present invention has been achieved in view of the above-mentioned problems, and an object of the invention is to provide a sterilizing method and apparatus which is harmless to the human body.

Another object of the invention is to provide a sterilizing method and apparatus, which exhibits superior sterilizing performance, and an air cleaning method and apparatus using the sterilizing method and apparatus.

In accordance with a first aspect, the present invention provides a sterilizing method which comprises: generating cations and anions using a cation generator and an anion generator, respectively; coupling electrons generated from the anion generator with the cations, thereby producing neutral atoms; and supplying the neutral atoms and anions to an object to be removed by sterilization, thereby removing the object by a sterilizing substance produced by coupling of the neutral atoms and anions.

In accordance with another aspect, the present invention provides a sterilizing method using a sterilizing apparatus including a cation generator, and an anion generator installed in the vicinity of the cation generator, the method comprising: driving the cation generator, thereby generating cations; driving the anion generator, thereby generating electrons and anions; moving the cations and electrons toward each other to cause the cations and electrons to react with each other, thereby producing neutral atoms; and moving the neutral atoms and anions toward an object to be removed by sterilization, to cause the neutral atoms and anions to react with the object, thereby producing a sterilizing substance.

In accordance with yet another aspect, the present invention provides a sterilizing apparatus comprising: a cation generator for generating cations; and an anion generator spaced apart from the cation generator by a predetermined distance for generating electrons and anions.

In accordance with yet another aspect, the present invention provides a sterilizing apparatus comprising: a first electrode for generating hydrogen ions in air; and a second electrode for generating electrons and super-oxide anions in the vicinity of the first electrode, wherein the hydrogen ions generated from the first electrode react with the electrons generated from the second electrode, thereby producing hydrogen atoms, which, in turn, react with the super-oxide anions generated from the second electrode, thereby killing bacteria present in the air.

In accordance with yet another aspect, the present invention provides a sterilizing apparatus comprising: a cation generator for generating cations in air; a neutral atom producer including an electron discharger for discharging electrons which react with the cations, thereby producing neutral atoms; and an anion generator for generating anions which react with the neutral atoms, thereby killing bacteria present in the air.

In accordance with yet another aspect, the present invention provides a sterilizing apparatus comprising: a first electrode for generating hydrogen ions in air; a second electrode for generating electrons in the vicinity of the first electrode; and a third electrode for generating super-oxide anions in the vicinity of the first and second electrodes, wherein the hydrogen ions generated from the first electrode react with the electrons generated from the second electrode, thereby producing hydrogen atoms which, in turn, react with the super-oxide anions generated from the third electrode, thereby killing bacteria present in the air.

In accordance with yet another aspect, the present invention provides an ion generating apparatus comprising: a cation generator for generating hydrogen ions in air; and an electron discharger arranged in the vicinity of the cation generator for discharging electrons, wherein the hydrogen ions generated from the cation generator react with the electrons discharged from the electron discharger, thereby producing hydrogen atoms which are, in turn, coupled with super-oxide anions present in the air, thereby removing the super-oxide anions.

In accordance with yet another aspect, the present invention provides an electric appliance comprising an air flow path, and a sterilizing apparatus arranged in the air flow path, wherein the sterilizing apparatus comprises: a first electrode for generating hydrogen ions in air; and a second electrode for generating electrons and super-oxide anions in the vicinity of the first electrode; wherein the hydrogen ions generated from the first electrode react with the electrons generated from the second electrode, thereby producing hydrogen atoms which, in turn, react with the super-oxide anions generated from the second electrode, thereby killing bacteria present in the air.

In accordance with another aspect, the present invention provides an air cleaning apparatus comprising: a filter arranged in a body; a blowing fan for circulating air present in a room space such that the air passes through the filter; an air discharge path for guiding the room air emerging from the filter to be discharged out of the body; and a sterilizer arranged in the air discharge path, the sterilizer including a cation generator and an anion generator.

Additional aspects and/or advantages of the invention will be set forth in the detailed description which follows.

BRIEF DESCRIPTION OF THE DRAWINGS

These and/or other aspects and advantages of the invention will become more apparent from the following description of the embodiments, taken in conjunction with the accompanying drawings in which.

DETAILED DESCRIPTION OF THE PREFERRED EMBODIMENTS

Reference will now be made in detail with respect to the embodiments of the present invention, examples of which are illustrated in the accompanying drawings, wherein like reference numerals refer to like elements throughout. The embodiments are described below to explain the present invention by referring to the figures. However, the present invention should not be construed as being limited thereto.

Figure 1:
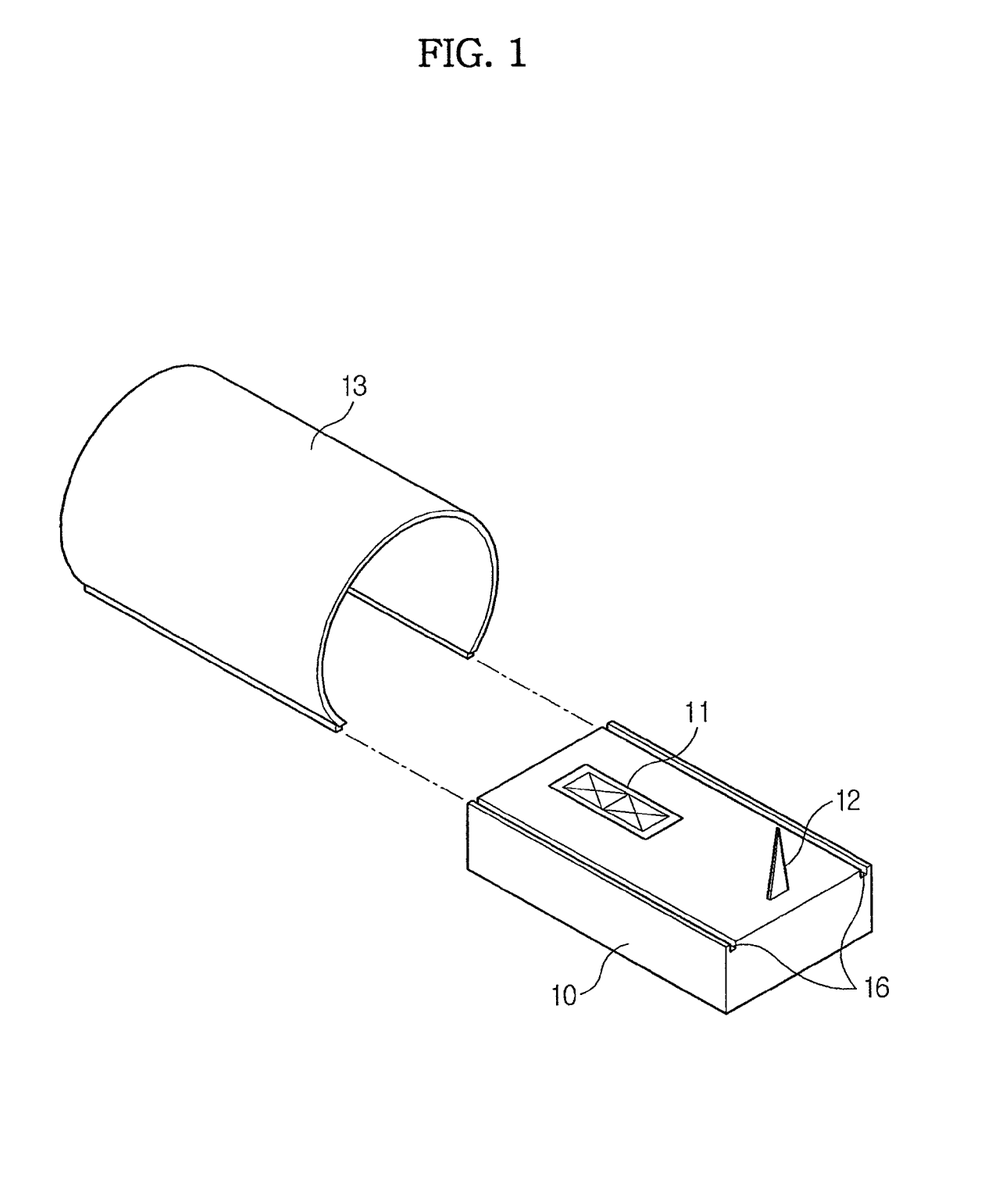
FIG. 1 is a perspective view illustrating a sterilizing apparatus according to a first embodiment of the present invention.
Figure 2:
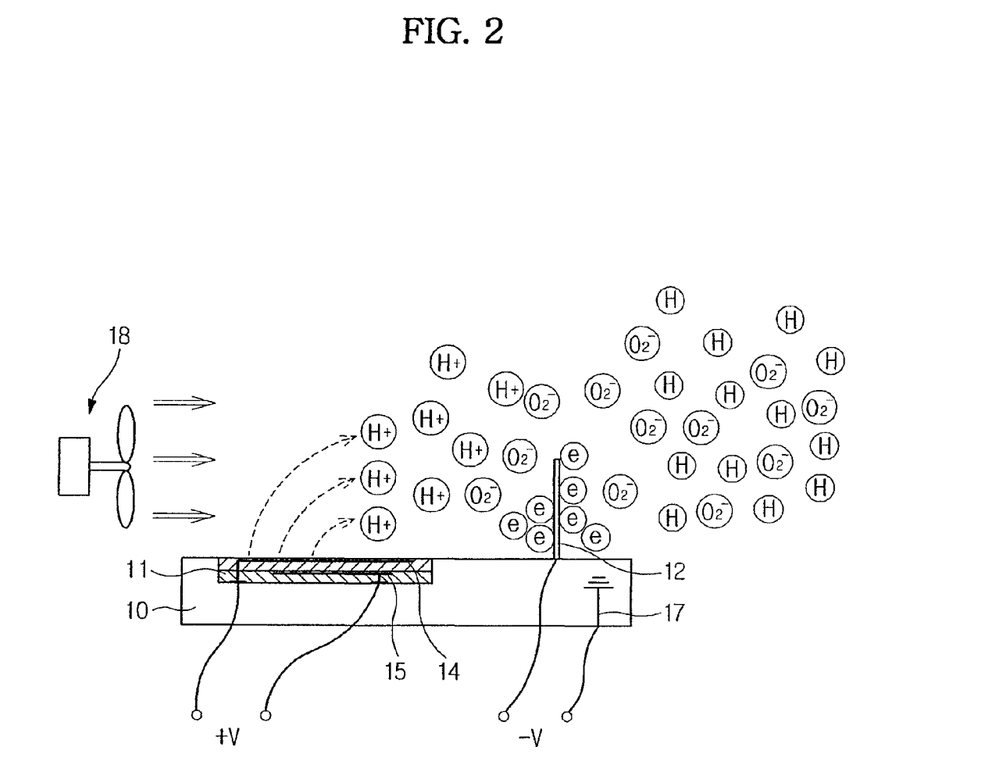
FIG. 2 is a schematic view showing ions generated from the sterilizing apparatus of FIG. 1.

FIGS. 1 and 2 illustrate a sterilizing apparatus according to a first embodiment of the present invention. As shown in FIGS. 1 and 2, the sterilizing apparatus includes a base 10, a ceramic plate 11 mounted on an upper surface of the base 10, a needle-shaped electrode 12 mounted on the base 10 while being spaced apart from the ceramic plate 11 by a predetermined distance, and a cover 13 which defines the diffusion range of ions generated from the ceramic plate 11 and needle-shaped electrode 12 within a predetermined space.

A recess is provided at the upper surface of the base 10 for mounting the ceramic plate 11. The ceramic plate 11 is fitted in the base 10. The ceramic plate 11 is adapted for generating cations. As shown in FIG. 2, a discharge electrode 14 is provided at an upper surface of the ceramic plate 11 inside the ceramic plate 11. An induction electrode 15 is also provided at a middle portion within the ceramic plate 11 when viewed in a thickness direction of the ceramic plate 11. The remaining portion of the ceramic plate 11 is made of ceramic to form a protective layer.

A high positive voltage is applied between the discharge electrode 14 and the induction electrode 15. The high positive voltage is preferably 3.9 kV to 4.3 kV, even though it may have other voltage ranges. When such a high positive voltage is applied between the discharge electrode 14 and the induction electrode 15, plasma discharge occurs at the ceramic plate 11, so that moisture ($H_2O$) present in the air around the ceramic plate 11 is ionized, thereby generating hydrogen ions ($H^+$).

Meanwhile, a high negative voltage is applied between the needle-shaped electrode 12 and a ground electrode 17. The high negative voltage is preferably −3.2 kV to −3.6 kV, even through it may have other voltage ranges. When such a high negative voltage is applied between the needle-shaped electrode 12 and the ground electrode 17, plasma discharge occurs at the needle-shaped electrode 12, so that cations accumulate around the needle-shaped electrode 12, and a large amount of electrons are discharged from the needle-shaped electrode 12 into the air. The electrons discharged into the air are very unstable and therefore are captured by oxygen molecules ($O_2$) in the air, thereby forming super-oxide anions ($O_2^-$). Thus, when a high negative voltage is applied to the needle-shaped electrode 12, electrons and super-oxide anions are generated.

Electrons discharged from the needle-shaped electrode 12 are coupled with hydrogen ions reaching the needle-shaped electrode 12 after being generated from the ceramic plate 11, so that hydrogen atoms (or active hydrogen) are produced. In order to promote coupling of the hydrogen ions, generated from the ceramic plate 11, with electrons generated from the needle-shaped electrode 12, a blower 18 may be arranged at one side of the sterilizing apparatus to forcibly feed hydrogen ions toward the needle-shaped electrode 12.

As described above, the needle-shaped electrode 12 is spaced apart from the ceramic plate 11 by a predetermined distance. It is desirable to appropriately determine the spacing between the ceramic plate 11 and the needle-spaced electrode 12, based on the size of the ceramic plate 11 and the height of the needle-shaped electrode 12. This is because the amount of hydrogen atoms formed from the hydrogen ions generated from the ceramic plate 11 varies depending on the spacing between the ceramic plate 11 and the needle-shaped electrode 12.

Since the hydrogen ions generated from the ceramic plate 11 are coupled with electrons discharged from the needle-shaped electrode 12, and thus, form hydrogen atoms, hydrogen atoms and super-oxide anions are finally discharged from the sterilizing apparatus.

The cover 13 has a tunnel-shaped structure opened at the bottom thereof to have a pair of laterally-spaced longitudinal lower ends. The cover 13 is separably coupled with the base 10 such that the lower ends of the cover 13 are slidably engaged with cover rails 16 formed at lateral ends of the base 10 on the upper surface of the base 10, respectively. When the sterilizing apparatus generates hydrogen ions while blowing air into the cover 13 at one side of the cover 13 under conditions in which the cover 13 is coupled with the base 10, the hydrogen ions thus generated are moved toward the needle-shaped electrode 12 within the cover 13 and the hydrogen ions are then coupled with electrons discharged from the needle-shaped electrode 12, thereby producing hydrogen atoms which are, in turn, discharged from the other side of cover 13. Together with the hydrogen atoms, super-oxide anions generated from the needle-shaped electrode 12 are also discharged from the other side of the cover 13 by the blowing air.

Hereinafter, a sterilizing method carried out by the sterilizing apparatus of FIG. 1 will be described with reference to FIGS. 3a to 3e.

Figure 3A:
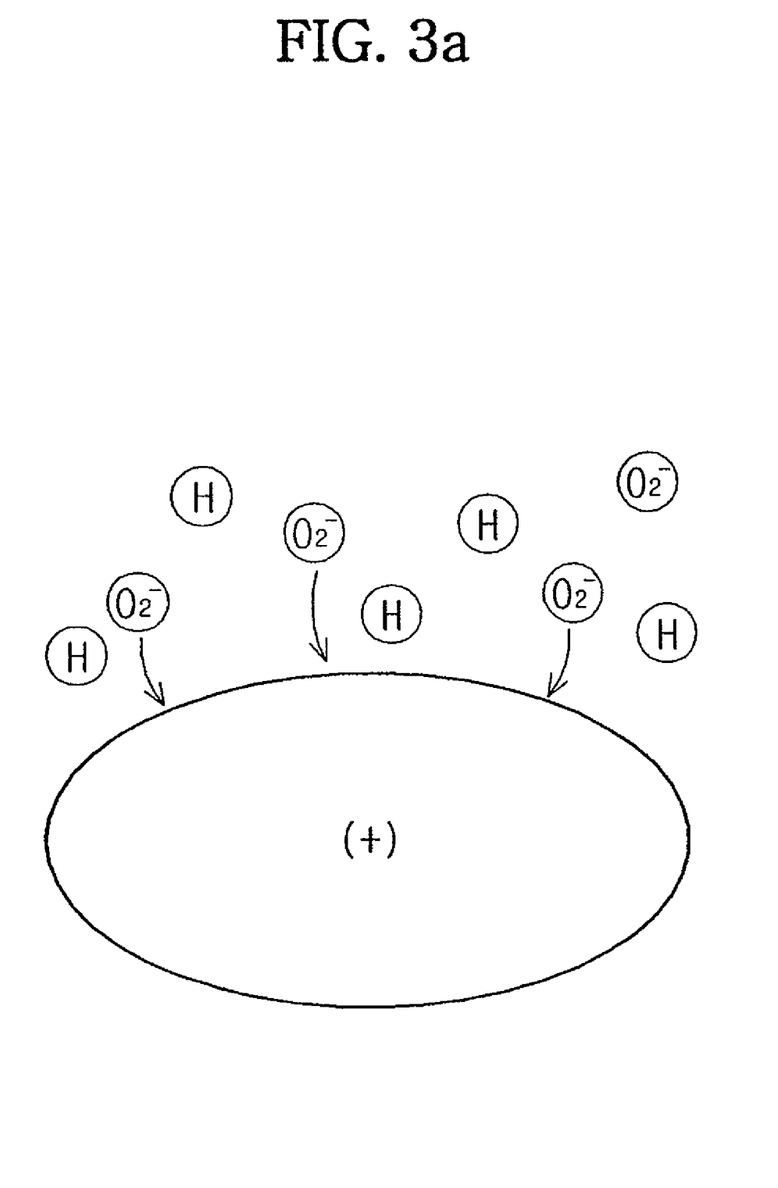
FIGS. 3a to 3e are schematic views showing a sterilizing method carried out by the sterilizing apparatus of FIG. 1.

In accordance with the sterilizing method, a high positive voltage is first applied between the discharge electrode 14 and induction electrode 15 in the ceramic plate 11, thereby generating hydrogen ions. Simultaneously, a high negative voltage is applied to the needle-shaped electrode 12, thereby generating electrons and super-oxide anions. Also, air is blown into the cover 13 at one side of the cover 13 to feed the hydrogen ions to the needle-shaped electrode 12 or a region around the needle-shaped electrode 12.

When the hydrogen ions approach the needle-shaped electrode 12, they are coupled with the electrons present around the needle-shaped electrode 12, thereby producing hydrogen atoms. The hydrogen atoms are then discharged from the cover 13, together with the super-oxide anions generated from the needle-shaped electrode 12.

Figure 3B:
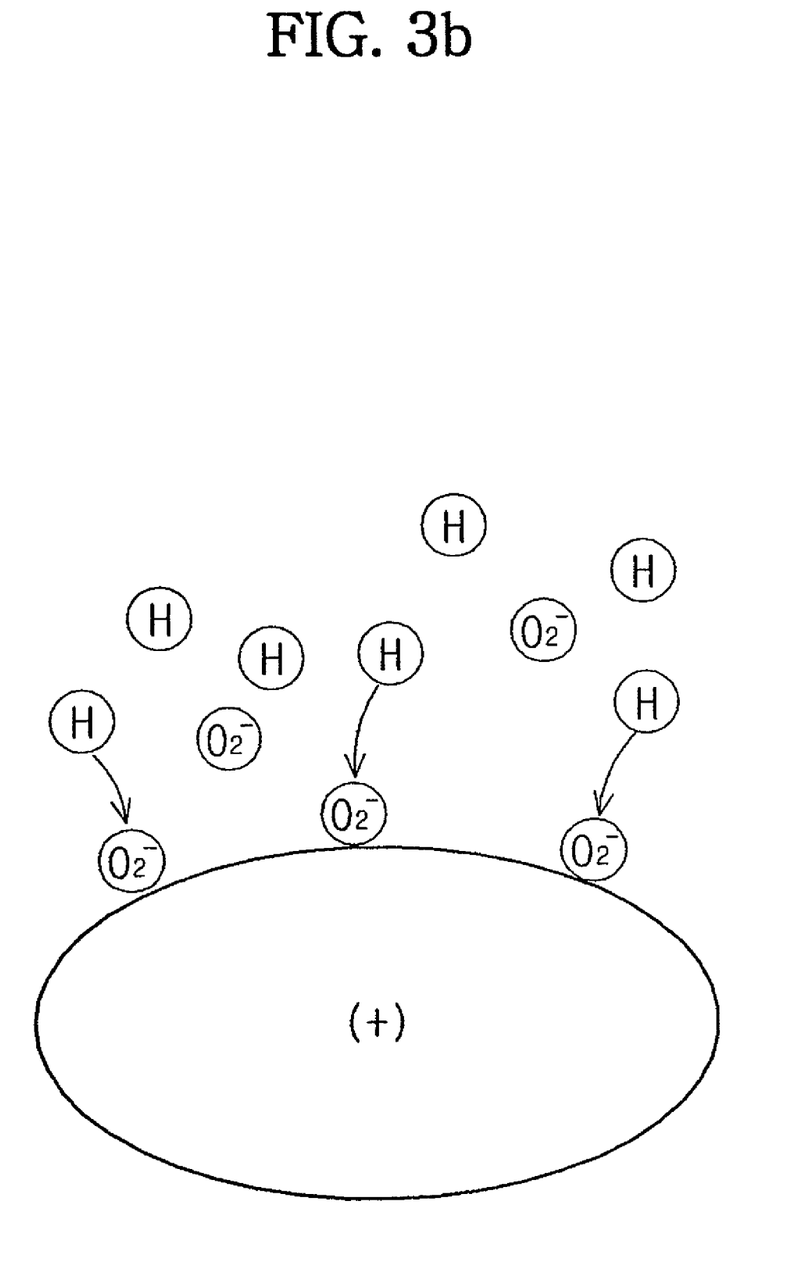
Figure 3C:
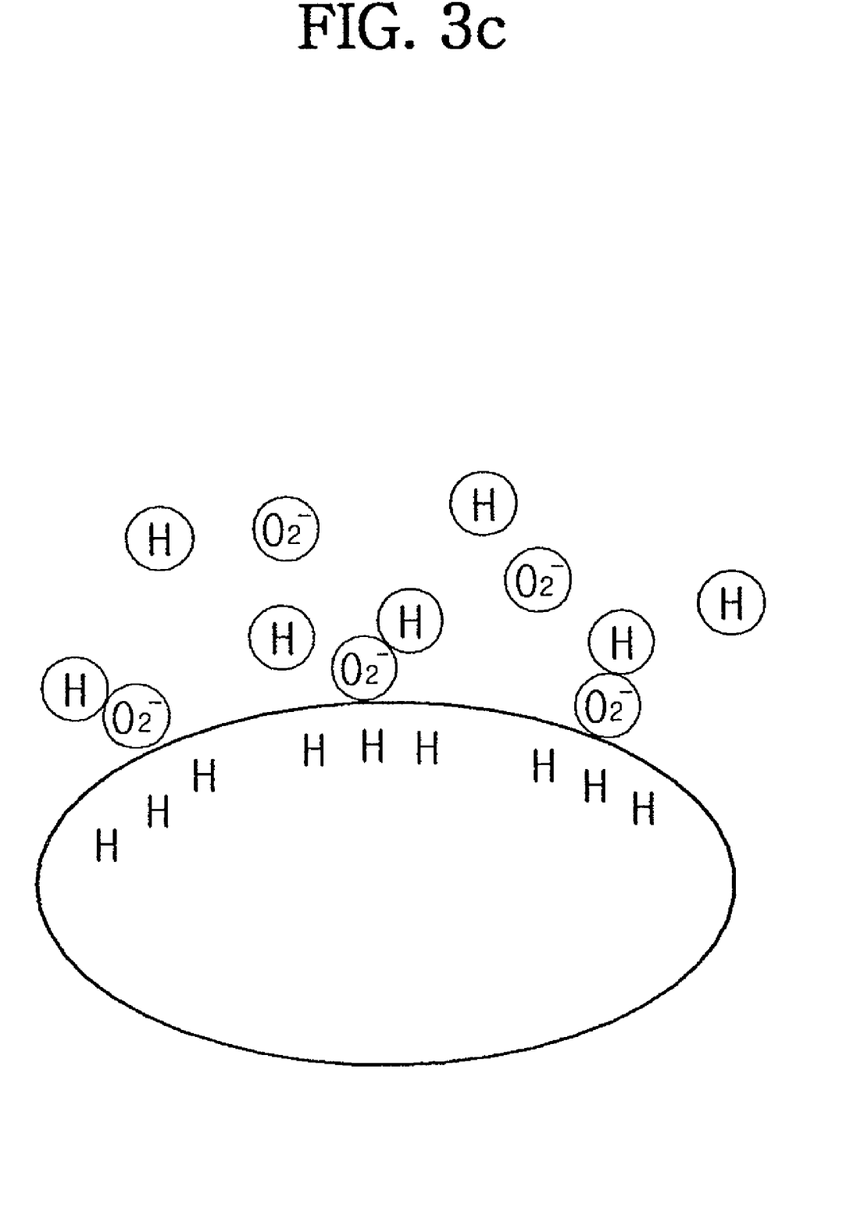

The super-oxide anions, which are discharged from the sterilizing apparatus into the air, exhibit a polarity opposite to static electricity (+) of bacteria floating in the air, so that the super-oxide anions are adsorbed to the surface of the bacteria, as shown in FIG. 3a. Once the super-oxide anions are adsorbed to the surface of the bacteria, the hydrogen atoms, which are discharged from the sterilizing apparatus into the air, react with the super-oxide anions, as shown in FIGS. 3b and 3c.

Figure 3D:
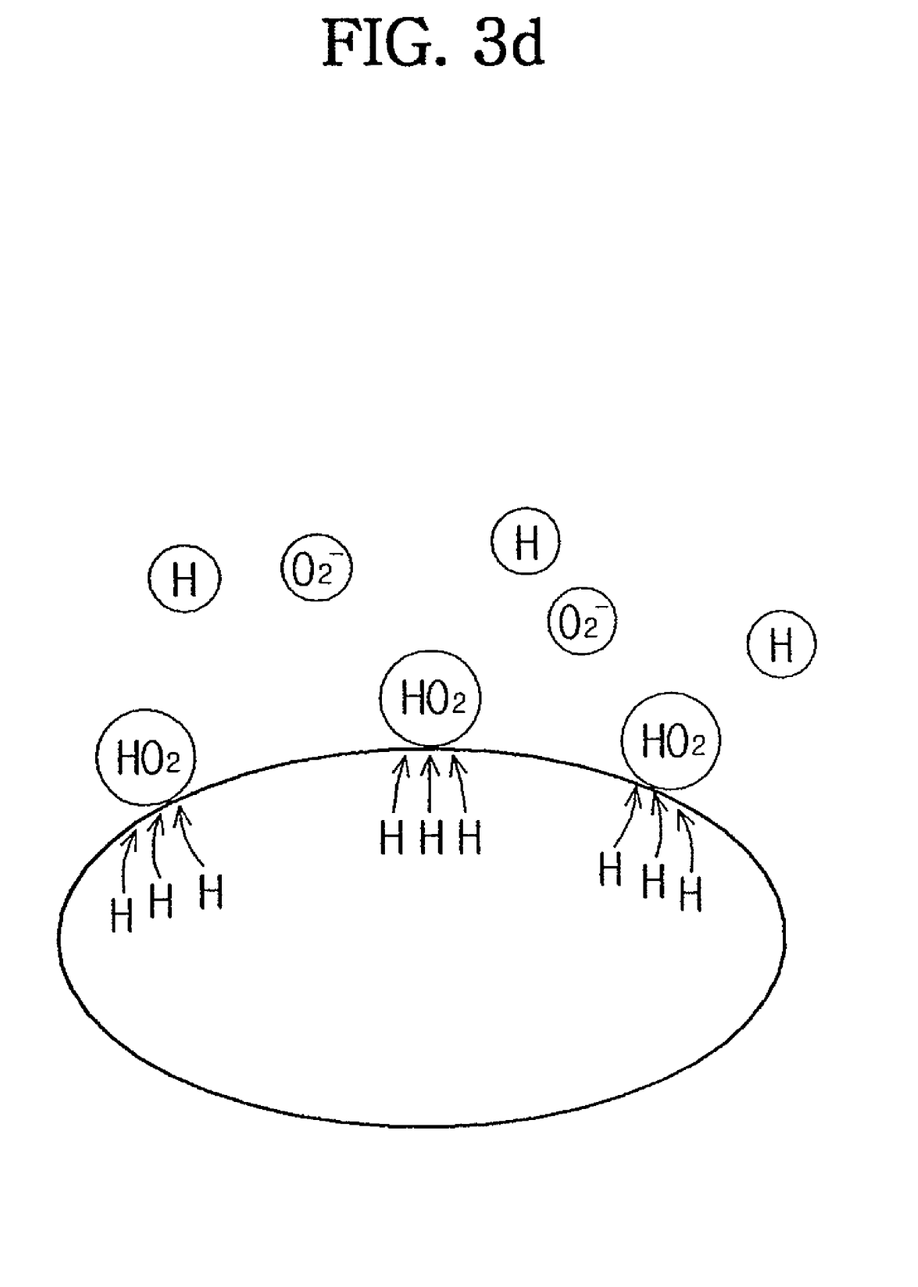
Figure 3E:
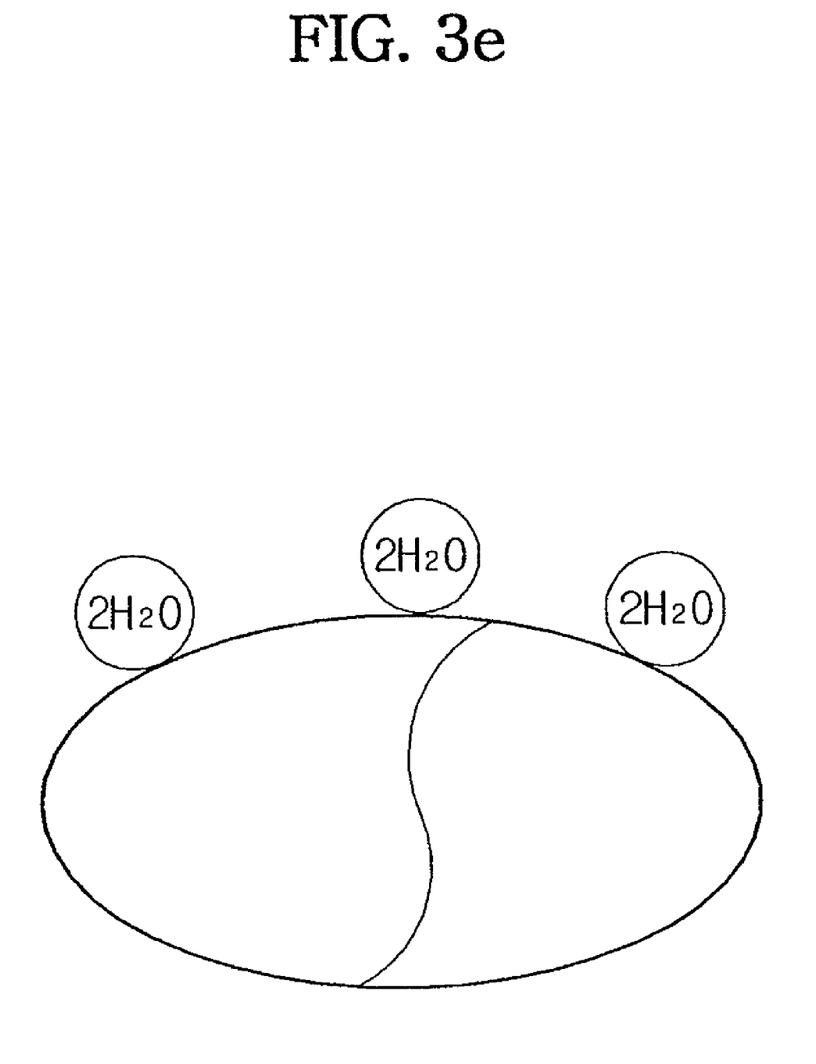

When such a reaction is carried out between the super-oxide anions and the hydrogen atoms, the following reactions are sequentially carried out, so that states of FIGS. 3d and 3e are sequentially obtained.

$H+O_2^- \rightarrow HO_2$ (hydroperoxy radical)+$e$+Static Electricity of Bacteria $HO_2+3H$ (hydrogen atoms of protein forming a cell membrane of the bacteria)$\rightarrow 2H_2O$ That is, the super-oxide anions and hydrogen atoms, which react with each other, form hydroperoxy radicals. Also, the electrons of the super-oxide anions offset the static electricity of the bacteria. Each hydroperoxy radical then captures three hydrogen atoms from the protein forming the cell membrane of the bacteria, thereby producing two water molecules. As a result, the protein molecules of the cell membrane, which donate the hydrogen atoms, are destroyed, thereby causing the cell membrane of the bacteria to be destroyed. Thus, sterilization is achieved.

Figure 4:
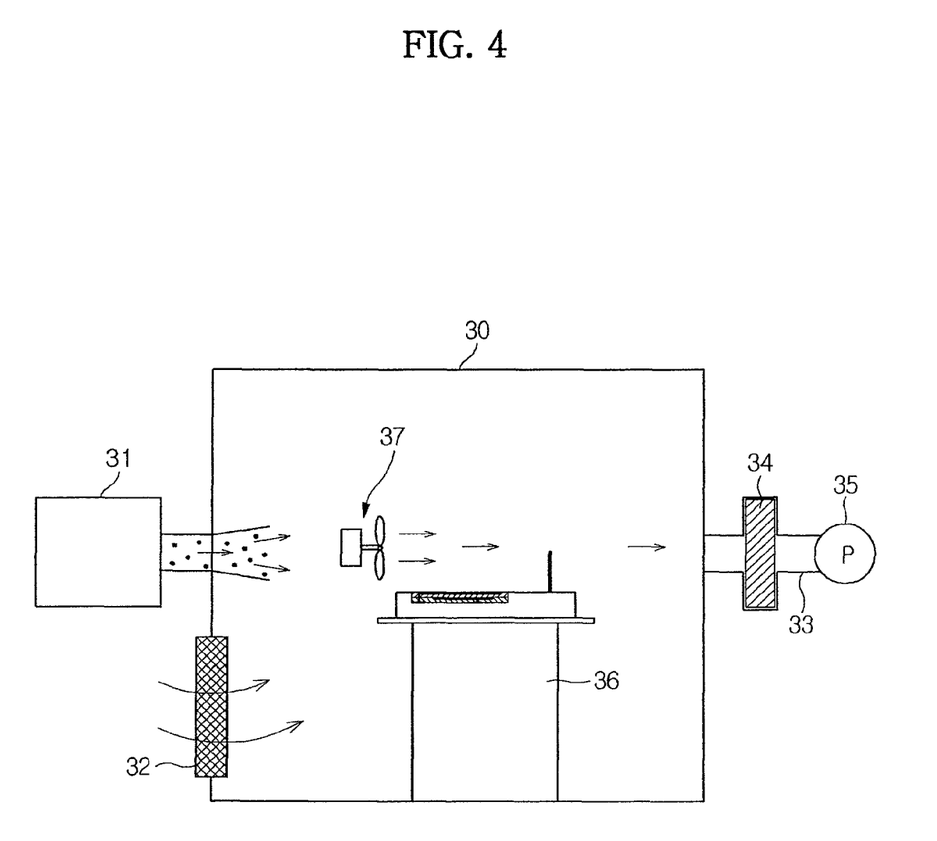
FIG. 4 is a schematic view illustrating a testing apparatus for testing the performance of the sterilizing apparatus shown in FIG. 1.
Figure 5:
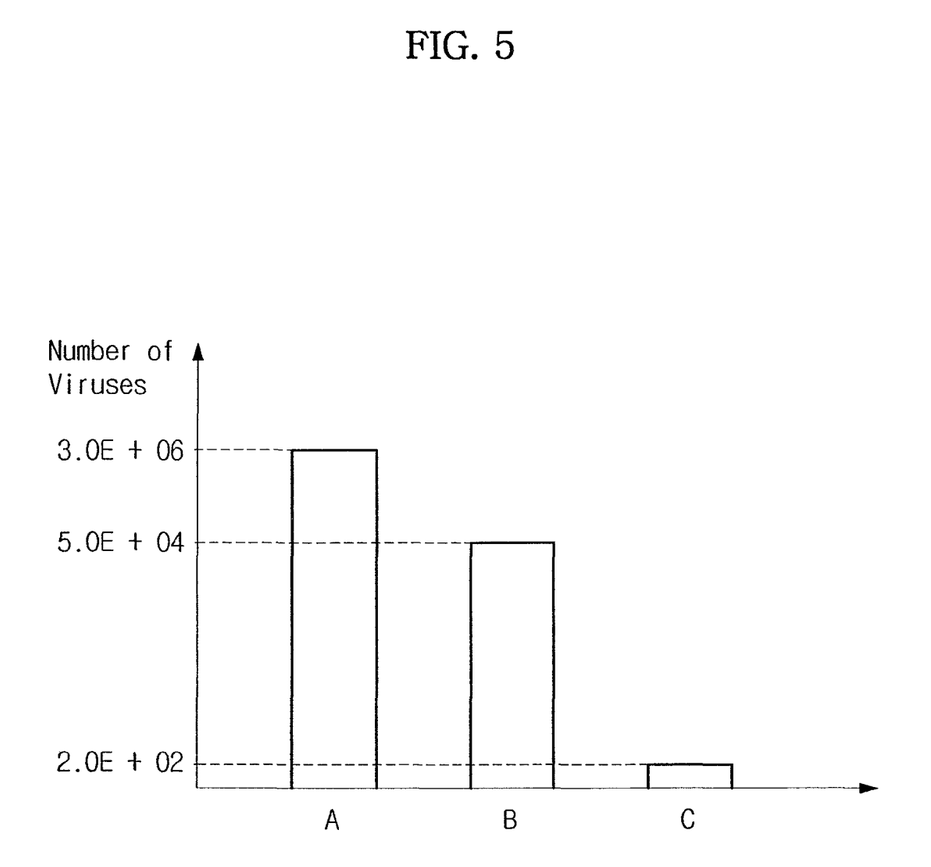
FIG. 5 shows graphs depicting the test results obtained by the testing apparatus of FIG. 4.
Figure 6:
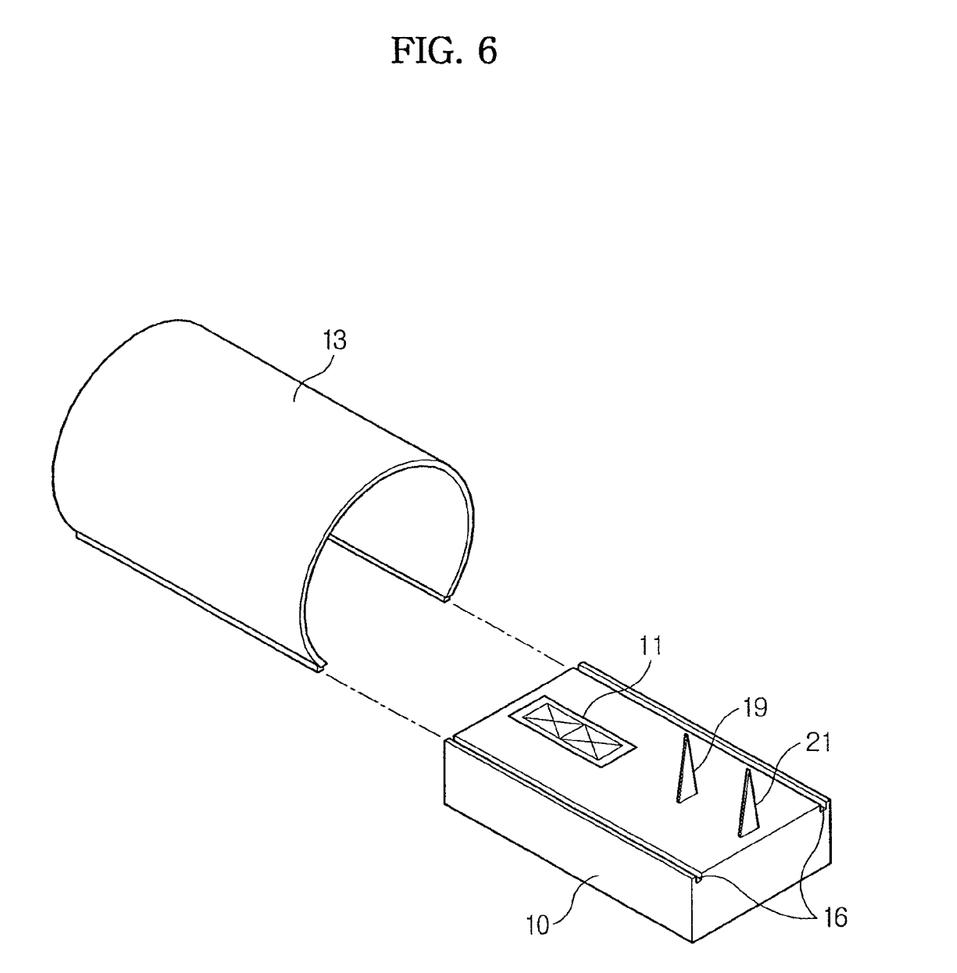
FIG. 6 is a perspective view illustrating a sterilizing apparatus according to a second embodiment of the present invention.

Referring to FIG. 4, an apparatus for testing the performance of the sterilizing apparatus shown in FIG. 1 is illustrated. The testing apparatus includes a chamber 30, a virus supplier 31 arranged at one side wall of the chamber 30, an ambient air sucking filter 32 arranged at one side wall of the chamber 30 beneath the virus supplier 31, and a discharge duct 33 connected to the other side wall of the chamber 30. A detection filter 34 is arranged in the discharge duct 33. A suction pump 35 is mounted to an outlet end of the discharge duct 33. A table 36, on which the sterilizing apparatus is to be laid for testing thereof, is arranged in the chamber 30. A blowing fan 37 is also arranged in the chamber 30 to blow air to the sterilizing apparatus.

For testing, the sterilizing apparatus is first laid on the table 36 in the testing apparatus. Thereafter, viruses (Influenza viruses, New Caledonia) are supplied from the virus supplier 31 into the chamber 30 for 10 minutes. After completion of the virus supply from the virus supplier 31, the sterilizing apparatus and blowing fan 37 are driven for 30 minutes. Subsequently, the suction pump 35 is driven. In this state, the number of viruses detected by the detection filter 34 is checked. FIG. 5 shows graphs respectively depicting the number of supplied viruses and the number of viruses detected by the detection filter 34.

In FIG. 5, the Y-axis represents the number of viruses (log scale), the graph A represents the number of viruses supplied from the virus supplier 31, the graph B represents the number of viruses detected after 30 minutes without driving the sterilizing apparatus, and the graph C represents the number of viruses detected after 30 minutes of driving the sterilizing apparatus. Referring to FIG. 5, it can be seen that the number of viruses was reduced when the sterilizing apparatus was not driven, however, the number of naturally reduced viruses was small. On the other hand, 99.6% of the supplied viruses were removed within 30 minutes when the sterilizing apparatus is driven.

Referring to FIGS. 6 and 7, a sterilizing apparatus according to a second embodiment of the present invention is illustrated. In FIGS. 6 and 7, constituent elements respectively corresponding to those in FIGS. 1 and 2 are denoted by the same reference numerals. As shown in FIGS. 6 and 7, the sterilizing apparatus includes a base 10, a ceramic plate 11 mounted on an upper surface of the base 10, a first needle-shaped electrode 19 mounted on the base 10 while being spaced apart from the ceramic plate 11 by a desired distance to generate electrons, a second needle-shaped electrode 21 mounted on the base 10 while being spaced apart from the first needle-shaped electrode 19 by a desired distance to generate super-oxide anions, and a cover 13 to define the diffusion range of ions generated from the ceramic plate 11 and needle-shaped electrodes 19 and 21 within a predetermined space. The ceramic plate 11 and cover 13 of FIG. 6 are the same as those of FIGS. 1 and 2, so that no description thereof will be given.

A high negative voltage of, for example, −3.2 kV to −3.6 kV, is applied between each of the first and second needle-shaped electrodes 19 and 21 and a ground electrode 17. When such a high negative voltage is applied between the first needle-shaped electrode 19 and the ground electrode 17, plasma discharge occurs at the first needle-shaped electrode 19, so that cations accumulate around the first needle-shaped electrode 19, and a large amount of electrons are discharged from the first needle-shaped electrode 19 into the air.

Since the first needle-shaped electrode 19 is arranged in the vicinity of the ceramic plate 11, the electrons discharged from the first needle-shaped electrode 19 are coupled with hydrogen ions reaching the first needle-shaped electrode 19 after being generated from the ceramic plate 11, so that hydrogen atoms (or active hydrogen) are produced. In order to promote the coupling of the hydrogen ions, generated from the ceramic plate 11, with the electrons generated from the first needle-shaped electrode 19, a blower 18 may be arranged at one side of the sterilizing apparatus to forcibly feed the hydrogen ions toward the first needle-shaped electrode 19.

Figure 7:
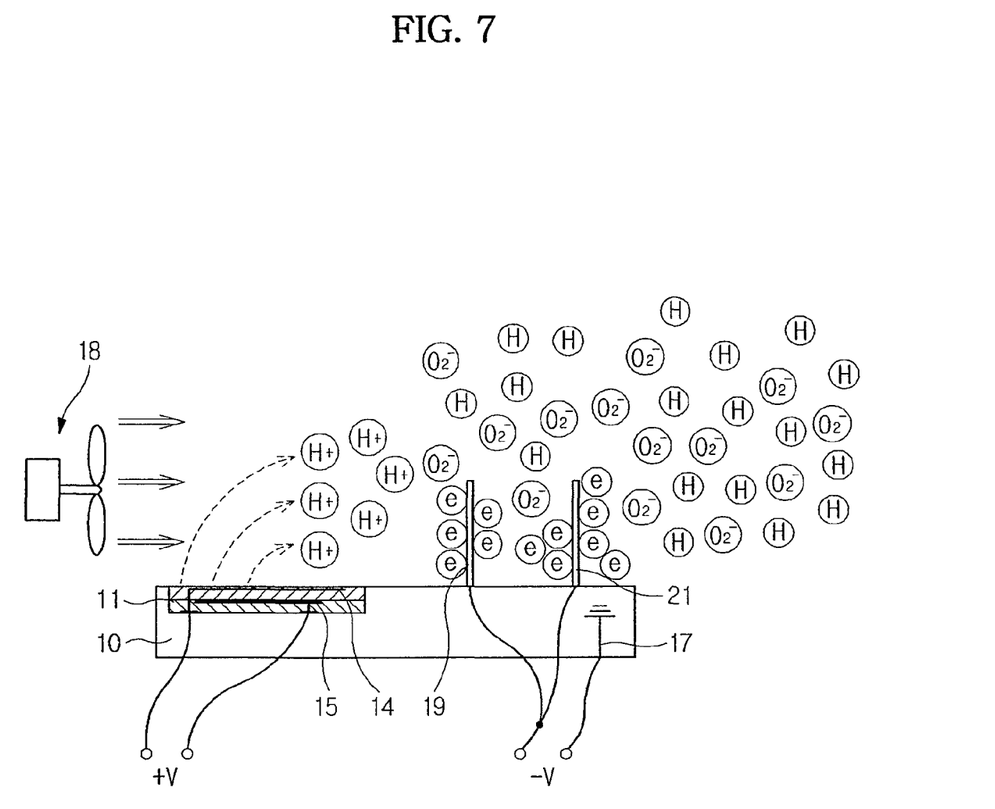
FIG. 7 is a schematic view showing ions generated from the sterilizing apparatus of FIG. 6.

Meanwhile, when the high negative voltage is applied between the second needle-shaped electrode 21 and the ground electrode 17, plasma discharge also occurs at the second needle-shaped electrode 21, so that a large amount of electrons are generated from the second needle-shaped electrode 21. Since the electrons discharged from the second needle-shaped electrode 21 into the air are very unstable, they are captured by oxygen molecules ($O_2$) in the air, thereby forming super-oxide anions ($O_2^-$).

Thus, the hydrogen ions discharged from the ceramic plate 11 are coupled with the electrons generated from the first needle-shaped electrode 19, thereby producing hydrogen atoms, The hydrogen atoms, in turn, react with the super-oxide anions generated from the second needle-shaped electrode 21, thereby producing hydroperoxy radicals having a sterilizing function. In accordance with the second embodiment of the present invention, hydrogen atoms are produced, using electrons generated from the first needle-shaped electrode 19, and super-oxide anions are generated from the second needle-shaped electrode 21, as compared to the first embodiment.

As described above, the first and second needle-shaped electrodes 19 and 21 are spaced apart from the ceramic plate 11 by predetermined distances, respectively. It is desirable to appropriately determine the spacing between the ceramic plate 11 and each needle-spaced electrode, based on the size of the ceramic plate 11 and the height of the needle-shaped electrode, to achieve maximal hydrogen atom producing performance.

Although the second embodiment of the present invention has been described in terms of a method in which a high negative voltage is applied to both the first and second needle-shaped electrodes 19 and 21, the high negative voltage may be applied to the first needle-shaped electrode 19 alone. In this case, hydrogen atoms, which are generated from the first needle-shaped electrode 19, are coupled with super-oxide anions, which are a kind of active oxygen naturally generated in the air, thereby removing the super-oxide anions.

Figure 8:
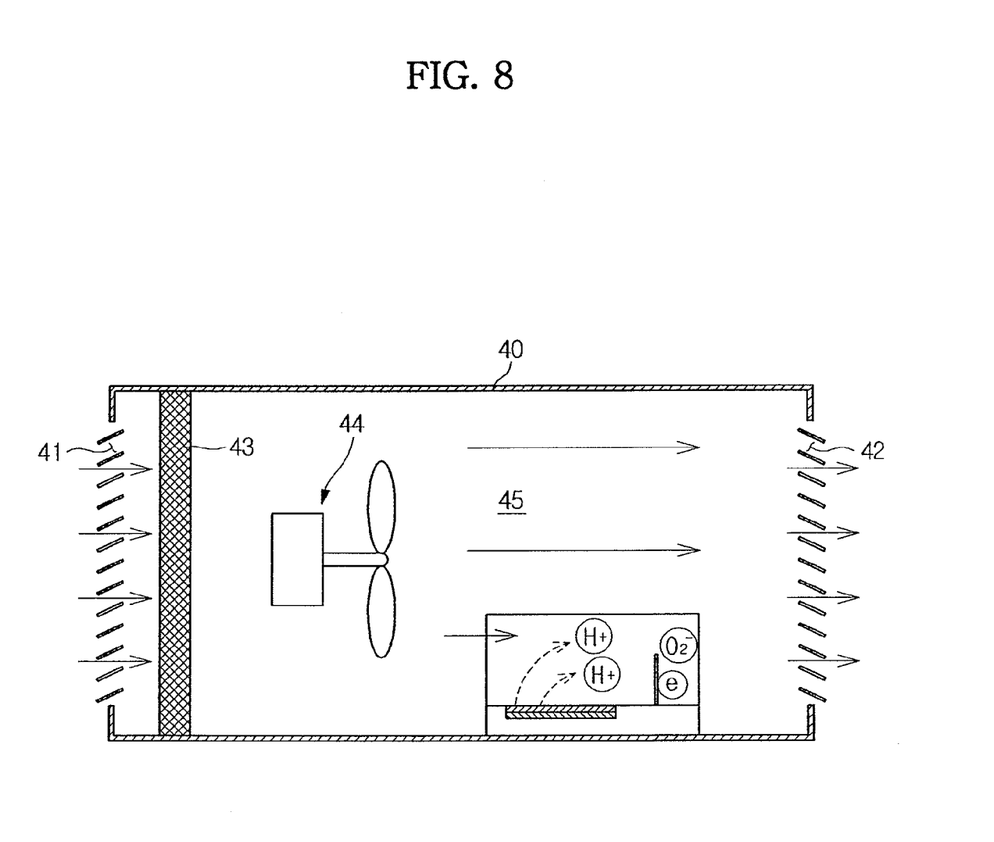
FIG. 8 is a schematic view illustrating an air cleaning apparatus in which the sterilizing apparatus of FIG. 1 is installed.

Referring to FIG. 8, an air cleaning apparatus is illustrated which uses the sterilizing apparatus of FIG. 1. The air cleaning apparatus includes a body 40, an inlet 41 arranged at one side wall of the body 40, an outlet 42 arranged at the other side wall of the body 40, a filter 43 mounted in the body 40, a blower 44 to forcibly circulate room air such that the room air is discharged out of the body 40 after passing through the filter 43, and the sterilizing apparatus of FIG. 1 arranged in an air discharge path 45 defined in the body 40.

When the blower 44 is driven to clean the room air in the air cleaning apparatus, the room air is sucked into the interior of the body 40 through the inlet 41, and then passes through the filter 43, so that impurities are removed from the room air by the filter 43. Thereafter, the room air is fed along the air discharge path 45 to be discharged out of the body 40 through the outlet 42. In this case, the sterilizing apparatus may be driven, simultaneously with the driving of the blower 44. When the sterilizing apparatus is driven, hydrogen atoms and super-oxide anions are discharged into the air discharge path 45. Accordingly, bacteria present in the room air passing through the air discharge path 45 are removed in accordance with the above-described sterilizing process using the generated hydrogen atoms and super-oxide anions.

Although this embodiment illustrates an air cleaning apparatus, to which the sterilizing apparatus is applied, the sterilizing apparatus of FIG. 1 and the sterilizing method using the same may also be applied to appliances requiring sterilization, other than air cleaners, for example, air conditioners, ventilators, and refrigerators.

Also, although hydrogen atoms and super-oxide anions are distributed into the air so that they are coupled in the air to produce hydroperoxy radicals for sterilization, in the illustrated embodiments, the hydroperoxy radicals themselves may be distributed into the air. In the latter case, the hydrogen atoms and super-oxide anions are coupled in the sterilizing apparatus to produce hydroperoxy radicals which are, in turn, distributed into the air.

In both the first and second embodiments of the present invention, the cover 13 is used to promote the reaction between hydrogen ions and electrons and the reaction between hydrogen atoms and super-oxide anions. However, the present invention may be implemented without using the cover 13.

As apparent from the above description, in accordance with the present invention, hydrogen atoms are used for sterilization, in place of hydrogen ions harmful to the human body. Accordingly, it is possible to prevent the user from being exposed to the harmful hydrogen ions during the sterilization.

In accordance with the present invention, the sterilizing apparatus includes a cation generator and an anion generator, which are separated from each other. Accordingly, it is possible to prevent a reduction in the number of ions available for sterilization due to ion loss caused by coupling of cations and anions prior to the use thereof for sterilization, as in conventional cases in which cations and anions are alternately generated from the same ion generator.

In addition, since the cation generator and anion generator are separated from each other, it is possible to produce a sufficient amount of ions required for sterilization, and thus, to achieve enhanced sterilizing performance.

Although certain embodiments of the present general inventive concept have been shown and described, it will be appreciated by those skilled in the art that changes may be made in these embodiments without departing from the principles and spirit of the invention, the scope of which is defined in the appended claims and their equivalents.

What is claimed is:

1. A method for sterilizing air using a sterilizing apparatus that includes a cation generator, and an anion generator, an inlet side into which air from a fan flows, and an outlet side from which anions are discharged, comprising:
    generating cations in the air using the cation generator, the cation generator being disposed at the inlet side; and
    generating electrons, using the anion generator, thereby killing bacteria present in the air, the anion generator being disposed at the outlet side.

2. A method of sterilizing air using an electric appliance having an air flow path, and a sterilizing apparatus arranged in the air flow path, comprising:
    blowing air from the air flow path into an inlet side of the sterilizing apparatus;
    generating hydrogen ions using a first electrode;
    generating electrons and super-oxide anions, with a second electrode, wherein the hydrogen ions generated from the first electrode react with the electrons generated from the second electrode, thereby producing hydrogen atoms which, in turn, react with the super-oxide anions generated from the second electrode, thereby killing bacteria present in the air; and
    discharging the hydrogen atoms and the super-oxide anions through an outlet side of the sterilizing apparatus, wherein said first electrode is disposed at the inlet side, and the second electrode is disposed at the outlet side.

3. A sterilizing method comprising:

generating hydrogen ions (H+) by use of a cation generator;

installing an anion generator to be spaced apart from the cation generator;

generating electrons and anions from the anion generator;

coupling the generated electrons and hydrogen ions, thereby producing hydrogen atoms (H);

flowing air in a direction from the cation generator toward the anion generator, to cause the hydrogen ions and the electrons to co-act; and supplying the hydrogen atoms and the anions to an object to be sterilized, thereby sterilizing the object.

4. The sterilizing method according to claim 3, wherein the anions comprise super-oxide anions ($O_2^-$).

5. The sterilizing method according to claim 4, wherein, when the super-oxide anions are supplied to the object to be sterilized, together with the hydrogen atoms, the super-oxide anions are adsorbed to the object by static electricity of the object, and the hydrogen atoms then react with the super-oxide anions, thereby producing hydroperoxy radicals.

* * * * *